US012655455B2

(12) United States Patent
Shapira et al.

(10) Patent No.: US 12,655,455 B2
(45) Date of Patent: Jun. 16, 2026

(54) METHODS AND SYSTEMS FOR LACTIC ACID PRODUCTION AND POLYLACTIC ACID RECYCLING

(71) Applicant: TRIPLEW LTD., Netanya (IL)

(72) Inventors: Tal Shapira, Even Yehuda (IL); Tsvika Greener, Ness Ziona (IL); Assaf J. Harnoy, Herzliya (IL)

(73) Assignee: TRIPLEW LTD., Netanya (IL)

( * ) Notice: Subject to any disclaimer, the term of this patent is extended or adjusted under 35 U.S.C. 154(b) by 882 days.

(21) Appl. No.: 17/800,898

(22) PCT Filed: Feb. 18, 2021

(86) PCT No.: PCT/IL2021/050189
§ 371 (c)(1),
(2) Date: Aug. 18, 2022

(87) PCT Pub. No.: WO2021/165964
PCT Pub. Date: Aug. 26, 2021

(65) Prior Publication Data
US 2023/0106737 A1        Apr. 6, 2023

Related U.S. Application Data

(60) Provisional application No. 62/978,338, filed on Feb. 19, 2020.

(51) Int. Cl.
| | |
|---|---|
| *C12P 7/56* | (2006.01) |
| *B29B 17/04* | (2006.01) |
| *C07C 51/41* | (2006.01) |
| *C08J 11/10* | (2006.01) |
| *C08J 11/16* | (2006.01) |
| *C12N 9/04* | (2006.01) |
| *C12P 41/00* | (2006.01) |

(52) U.S. Cl.
CPC ............... *C12P 7/56* (2013.01); *B29B 17/04* (2013.01); *C07C 51/412* (2013.01); *C08J 11/105* (2013.01); *C08J 11/16* (2013.01); *C12N 9/0006* (2013.01); *C12P 41/001* (2013.01); *C12Y 101/01028* (2013.01); *C08J 2367/04* (2013.01)

(58) Field of Classification Search
None
See application file for complete search history.

(56) References Cited

U.S. PATENT DOCUMENTS

| | | | |
|---|---|---|---|
| 7,985,778 | B2 | 7/2011 | Nakamura |
| 8,431,683 | B2 | 4/2013 | Coszach |
| 8,481,675 | B2 | 7/2013 | Coszach |
| 8,614,338 | B2 | 12/2013 | Coszach |
| 8,895,778 | B2 | 11/2014 | Srinivasan |
| 2014/0360728 | A1* | 12/2014 | Tashiro .................. C09K 8/805 166/305.1 |

| | | | |
|---|---|---|---|
| 2017/0218408 | A1 | 8/2017 | Baets |
| 2017/0292133 | A1 | 10/2017 | Baets |
| 2018/0051156 | A1 | 2/2018 | Foley |
| 2019/0024125 | A1* | 1/2019 | Kalbasenka .............. C12P 7/56 |

FOREIGN PATENT DOCUMENTS

| | | | |
|---|---|---|---|
| CN | 103074384 | A | 5/2013 |
| CN | 109761798 | A * | 5/2019 |
| ES | 2311024 | T3 | 2/2009 |
| IN | 240637 | B | 5/2007 |
| JP | S60217897 | A | 10/1985 |
| JP | 2001232331 | A | 8/2001 |
| JP | 2004339420 | A | 12/2004 |
| JP | 2005206735 | A | 8/2005 |
| JP | 2005232336 | A | 9/2005 |
| KR | 20010031102 | A | 4/2001 |
| WO | 2014087984 | A1 | 6/2014 |
| WO | 2015021356 | A1 | 2/2015 |
| WO | 2015112098 | A1 | 7/2015 |
| WO | 2017122197 | A1 | 7/2017 |
| WO | 2020110108 | A1 | 6/2020 |
| WO | 2020208635 | A1 | 10/2020 |

OTHER PUBLICATIONS

Yagihashi et al., Recovery of L-Lactic Acid from Poly(L-lactic acid) under Hydrothermal Conditions of Dilute Aqueous Sodium Hydroxide Solution, Ind. Eng. Chem. Res. 49, 2010, 1247-51. (Year: 2010).*

Akerberg et al., Modelling the influence of pH, temperature, glucose and lactic acid concentrations on the kinetics of lactic acid production by *Lactococcus lactis* ssp. lactis ATCC 19435 in whole-wheat flour, Appl. Microbiol. Biotechnol. 49, 1998, 682-90. (Year: 1998).*

Quintero et al., Purification of lactic acid obtained from a fermentative process of cassava syrup using ion exchange resins, Rev. Fac. Ing. Univ. Antioquira 65, 2012, 129-51. (Year: 2012).*

Chauliac et al., Removing chiral contamination of lactate solutions by selective metabolism of the D-enantiomer, Biotechnol. Lett 37, 2015, 2411-18. (Year: 2015).*

Sheng et al., Enzymatic Resolution by a d-Lactate Oxidase Catalyzed Reaction for (S)-2-Hydroxycarboxylic Acids, ChemCatChem 8, 2016, 2630-33. (Year: 2016).*

Piemonte et al., Chemical Recycling of Pla, J. Polym. Environ. 21, 2013, 640-47. (Year: 2013).*

Li et al., (2017) Enzymatic Cascades for Efficient Biotransformation of Racemic Lactate Derived from Corn Steep Water. ACS Sustainable Chem Eng 5(4): 3456-3464.

Hideki Yamane (2007) Bio-Based Polymers I: New Developments of Poly (lactic Acid). Journal of the Society of Materials Science, Japan 56(10): 993-997. With machine translation.

Anneaux et al., (2018) A Novel Method for Chemical Recycling of PLA Under Mild Conditions. Zeus Industrial Products, Inc. Orangeburg, SC, May 1, 2018. 10 pages.

(Continued)

*Primary Examiner* — Todd M Epstein
(74) *Attorney, Agent, or Firm* — Fuller IP Law LLC; Rodney J. Fuller

(57) ABSTRACT

Industrial fermentation for the production of lactic acid from organic waste combined with chemical recycling of polylactic acid are provided, to obtain lactic acid at high yields.

16 Claims, 4 Drawing Sheets

(56)        References Cited

OTHER PUBLICATIONS

Cam et al., (1995) Degradation of high molecular weight poly(L-lactide) in alkaline medium. Biomaterials 16(11): 833-843.

Chauliac (2013) Development of a thermochemical process for hydrolysis of polylactic acid polymers to L-lactic acid and its purification using an engineered microbe Ph.D. thesis, University of Florida, USA. UMI No. 3583516. 124 pages.

Dusselier et al., (2015) Green Chemistry. Shape-selective zeolite catalysis for bioplastics production. Science 349 (6243): 78-80.

Elsawy et al. (2017) Hydrolytic degradation of polylactic acid (PLA) and its composites. Renewable and Sustainable Energy Reviews 79: 1346-1352.

Ghaffar et al., (2014) Recent trends in lactic acid biotechnology: A brief review on production to purification. Journal of Radiation Research and Applied Sciences 7(2): 222-229.

Liu et al., (2013) Alkaline twin-screw extrusion pretreatment for fermentable sugar production. Biotechnology for Biofuels 6: Article No. 97.

López-Garzón and Straathof (2014) Recovery of carboxylic acids produced by fermentation. Biotechnol Adv 32(5): 873-904.

McKeown et al., (2020) The Chemical Recycling of PLA: A Review. Sustain Chem 1(1): 1-22.

Mobedi et al., (2006) Studying the Degradation of Poly(L-lactide) in Presence of Magnesium Hydroxide. Iranian Polymer Journal 15(1): 31-39.

Motoyama et al., (2007) Effects of MgO catalyst on depolymerization of poly-l-lactic acid to l,l-lactide. Polymer Degradation and Stability 92(7): 1350-1358.

Siparsky et al., (1998) Hydrolysis of Polylactic Acid (PLA) and Polycaprolactone (PCL) in Aqueous Acetonitrile Solutions: Autocatalysis. Journal of environmental polymer degradation 6(1): 31-41.

Wadso and Karlsson (2013) Alkaline hydrolysis of polymers with ester groups studied by isothermal calorimetry. Polymer Degradation and Stability 98(1): 73-78.

Xu et al., (2011) Effects of Temperature and pH on the Degradation of Poly(lactic acid) Brushes. Macromolecules 44 (12): 4777-4782.

Lactic_Acid_Titration_Extension, Recycling Polylactic Acid (PLA)—Student Guide. retrieved from https://www.beyondbenign.org/lessons/recycling-polylactic-acid/ May 15, 2018 (May 15, 2018). 11 pages.

Lactic_Acid_Titration_Extension, Green Chemistry & Sustainable Science. retrieved from https://www.beyondbenign.org/lessons/recycling-polylactic acid/ May 15, 2018 (May 15, 2018). 13 pages.

Hottle et al., (2016) Alkaline Amendment for the Enhancement of Compost Degradation for Polylactic Acid Biopolymer Products. Compost Science & Utilization 24(3): 159-173.

Vaidya et al., (2005) Production and Recovery of Lactic Acid for Polylactide—An Overview. Critical Reviews in Environmental Science and Technology 35(5): 429-467.

* cited by examiner

METHODS AND SYSTEMS FOR LACTIC ACID PRODUCTION AND POLYLACTIC ACID RECYCLING

CROSS-REFERENCE TO RELATED APPLICATIONS

This application is the U.S. National Stage of International Patent Application No. PCT/IL2021/050189, filed on Feb. 18, 2021, which claims the benefit of and priority to U.S. Provisional Patent Application No. 62/978,338, filed on Feb. 19, 2020, the contents of each of which are hereby incorporated by reference in their entireties.

FIELD OF THE INVENTION

The present invention relates to dual recycling of organic waste and polylactic acid. In particular, there is provided methods and systems for recycling of organic waste to lactic acid combined with chemical recycling of polylactic acid (PLA).

BACKGROUND OF THE INVENTION

Lactic Acid Fermentation

Lactic acid fermentation, namely, production of lactic acid from carbohydrate sources via microbial fermentation, has been gaining interest in recent years due to the ability to use lactic acid as a building block in the manufacture of bioplastics. Lactic acid can be polymerized to form the biodegradable and recyclable polyester, polylactic acid (PLA), which is considered a potential substitute for plastics manufactured from petroleum. PLA is used in the manufacture of various products including food packaging, disposables, fibers in the textile and hygiene products industries, and more.

Production of lactic acid by fermentation bioprocesses is preferred over chemical synthesis methods for various considerations, including environmental concerns, costs and the difficulty to generate enantiomerically pure lactic acid by chemical synthesis, which is desired for most industrial applications. The conventional fermentation process is typically based on anaerobic fermentation by lactic acid-producing microorganisms, which produce lactic acid as the major metabolic end product of carbohydrate fermentation. For production of PLA, the lactic acid generated during the fermentation is separated from the fermentation broth and purified by various processes, and the purified lactic acid is then subjected to polymerization.

Lactic acid has a chiral carbon atom and therefore exists in two enantiomeric forms, D- and L-lactic acid. In order to generate PLA that is suitable for industrial applications, the D- or L-lactic acid entering the production process must be highly purified to meet the specification required for polymerization. In addition, lactic acid bacteria that produce only L-lactate enantiomer or only D-lactate enantiomer are typically used in order to produce one discreet enantiomer (L or D).

In currently available commercial processes, the carbohydrate source for lactic acid fermentation is typically a starch-containing renewable source such as corn and cassava root. Additional sources, such as the cellulose-rich sugarcane bagasse, have also been proposed. Typically, lactic acid bacteria can utilize reducing sugars like glucose and fructose, but do not have the ability to degrade polysaccharides like starch and cellulose. Thus, to utilize such polysaccharides, the process requires adding glycolytic enzymes, typically in combination with chemical treatment, to degrade the polysaccharides and release reducing sugars.

An additional source of carbohydrates for lactic acid fermentation that has been proposed is complex organic waste, such as mixed food waste from municipal, industrial and commercial origin. Organic waste is advantageous as it is readily available and less expensive compared to other carbohydrate sources for lactic acid fermentation.

Mixed food waste typically includes varied ratios of reducing sugars (glucose, fructose, lactose, etc.), starch and lignocellulosic material. Mixed food waste also contains endogenous D,L-lactic acid (e.g., from dairy products or natural decomposition during transportation), one of which needs to be removed in order to utilize the waste as a substrate for producing optically pure lactic acid (L- or D-lactic acid). WO 2017/122197, assigned to the Applicant of the present invention, discloses dual action lactic-acid (LA)-utilizing bacteria genetically modified to secrete polysaccharide-degrading enzymes such as cellulases, hemicellulases, and amylases, useful for processing organic waste both to eliminate lactic acid present in the waste and degrade complex polysaccharides.

Organic waste such as mixed food waste is also characterized by high variability in terms of carbohydrate content, and its composition varies from batch to batch where some batches may be rich in carbohydrates compared to others that have a low carbohydrate content. Thus, lactic acid fermentation processes based on organic waste may result in yields that vary from one batch to another, and in certain instances very low yield of lactic acid is obtained.

Polylactic Acid (PLA) Recycling

PLA produced from renewable resources is an alternative to petroleum-derived plastics, and its use in the manufacture of products such as food packaging is continuously growing. Due to the increasing presence of PLA in disposable end products it is important to ensure that PLA is adequately addressed after disposal. Unlike thermoplastic resins such as polyethylene, polypropylene, polystyrene and poly(ethylene terephthalate), PLA is subject to thermal degradation. Accordingly, when products containing a mixture of PLA and the aforementioned plastics are recycled, it is desirable to separate PLA in order to avoid contamination of the recycling streams.

Recycling options for PLA include landfilling, composting, anaerobic digestion (biogas production), incineration and chemical recycling into the constituent monomers. Chemical recycling is preferred over other methods as the monomers can be reused in the production of new PLA.

One of the common forms of PLA on the market is the copolymer PDLLA (Poly (D-L-)lactic acid), predominantly composed of PLLA (made from L-lactic acid), and small amounts of PDLA (made from D-lactic acid). A significant portion of the PLA plastics present on the market contains a small amount of PDLA that when hydrolyzed, releases D-lactic acid. The hydrolyzed material may also contain unknown amounts of D-LA formed by racemization during the hydrolysis. An optical purity of over 99% is typically required for both D-lactic acid and L-lactic acid entering the PLA production process. Therefore, PLA recycling processes should address the issue of isomer separation. Chemical separation of the two enantiomers is expensive, usually using liquid or solid enantioselective membranes or high-performance liquid chromatography (HPLC).

Cam, Hyon and Ikada (1995) *Biomaterials,* 16(11): 833-43, report the degradation of high molecular weight poly(L-lactide) in alkaline medium. The study tested the effect of molecular weight and morphology on hydrolytic degrada-
tion. Degradation was performed at 37° C. in 0.01 N NaOH
solution.

Siparsky, Voorhees, and Miao (1998) *Journal of environ-
mental polymer degradation,* 6(1): 31-41, report the hydro-
lysis of polylactic acid (PLA) and polycaprolactone (PCL)
in aqueous acetonitrile solutions.

Xu, Crawford and Gorman (2011) *Macromolecules,*
44(12): 4777-4782, report the effects of temperature and pH
on the degradation of poly(lactic acid) brushes.

Chauliac (2013) "Development of a thermochemical pro-
cess for hydrolysis of polylactic acid polymers to L-lactic
acid and its purification using an engineered microbe" *Ph.D.
thesis, University of Florida,* UMI Number: 3583516, pro-
poses a process for post-consumer use of PLA polymers. In
this process, thermohydrolysis is the first step, followed by
D-LA removal from the hydrolyzed material to yield pure
L-LA that could be redirected into the production of the
polymer itself. Thermohydrolysis was performed with water
in the presence of NaOH. D-LA removal from the resulting
syrup was achieved using an *Escherichia coli* lacking all
three L-lactate dehydrogenases identified.

Wadsö and Karlsson (2013) *Polymer Degradation and
Stability,* 98(1): 73-78, report two studies to measure the
enthalpy of alkaline hydrolysis of polymers containing
esters of carboxylic acids. Two materials were used: poly
(vinyl acetate), PVAc, films and poly(lactic acid), PLA,
fibers. Degradation was carried out using sodium hydroxide
and potassium hydroxide at 30° C.

Elsawy et al. (2017) *Renewable and Sustainable Energy
Reviews,* 79: 1346-1352, review the hydrolytic degradation
of polylactic acid (PLA) and its composites.

Motoyama et al. (2007) *Polymer Degradation and Sta-
bility,* 92(7): 1350-1358, report the effects of MgO catalyst
on depolymerization of poly-L-lactic acid to L,L-lactide.

WO 2015/112098 discloses a process for manufacturing
lactide from plastics having polylactic acid (PLA-based
plastics) that comprises preparing PLA-based plastics,
accelerating decomposition of polylactic acid in the plastics
by alcoholysis or hydrolysis to provide low molecular
weight polylactic acid, and thermal decomposition of the
low molecular weight polylactic acid to provide lactide.
Also, the process further comprises minimizing the size of
the PLA-based plastics after the preparation step, and puri-
fying lactide after thermal decomposition of the low molecu-
lar weight polylactic acid.

U.S. Pat. No. 7,985,778 discloses a method for decom-
posing and reclaiming synthetic resin having ester bond in
composition structure thereof, by conducting hydrolysis
treatment and then separation collection treatment. In the
hydrolysis treatment, an article containing synthetic resin to
be decomposed and reclaimed is exposed to water vapor
atmosphere filled under saturation water vapor pressure at
treatment temperature at or below melting point of the
synthetic resin. The synthetic resin in article to be treated is
hydrolyzed by water vapor generated at the treatment tem-
perature, to generate decomposition product before polym-
erizing to the synthetic resin containing an ester bond. The
separation collection treatment is treatment in which the
decomposition product generated by the hydrolysis treat-
ment is separated into liquid component and solid compo-
nent to be collected individually.

U.S. Pat. No. 8,614,338 discloses a method for the
stereospecific chemical recycling of a mixture of polymers
based on polylactic acid PLA, in order to reform the
monomer thereof or one of the derivatives thereof. The
method comprises a step of putting the mixture of polymers in suspension in a lactic ester able to dissolve the PLA
fraction followed by a separation firstly of the lactic ester,
the PLA and other dissolved impurities and secondly the
mixture of other polymers and impurities that are insoluble.
The solution containing the PLA thus obtained is then
subjected to a catalytic depolymerization reaction by trans-
esterification in order to form oligoesters. The depolymer-
ization reaction by transesterification is then stopped at a
given moment and the residual lactic ester separated. The
oligoester thus obtained then undergoes a cyclisation reac-
tion in order to produce lactide that will finally be purified
stereospecifically so as to obtain a fraction of purified lactide
having a meso-lactide content of between 0.1% and 40%.

U.S. Pat. Nos. 8,431,683 and 8,481,675 disclose a process
for recycling a polymer blend necessarily containing PLA,
comprising grinding, compacting, dissolving in a solvent of
PLA, removing the undissolved contaminating polymers,
alcoholysis depolymerization reaction and purification
steps.

U.S. Pat. No. 8,895,778 discloses depolymerization of
polyesters such as post-consumer polylactic acid. Ultrasonic
induced implosions can be used to facilitate the depolymer-
ization. Post-consumer PLA was exposed to methanol as the
suspension media in the presence of organic or ionic salts of
alkali metals such a potassium carbonate and sodium
hydroxide as depolymerization catalysts to provide high
quality lactic acid monomers in high yield.

U.S. 2018/0051156 disclose a method for enhancing/
accelerating the depolymerization of polymers (e.g., those
containing hydrolyzable linkages), the method generally
involves contacting a polymer comprising hydrolyzable
linkages with a solvent and an alcohol to give a polymer
mixture in which the polymer is substantially dissolved,
wherein the contacting is conducted at a temperature at or
below the boiling point of the polymer mixture. A resulting
depolymerized polymer can be separated therefrom (includ-
ing, e.g., monomers and/or oligomers). Such methods can be
conducted under relatively mild temperature and pressure
conditions. In some embodiments, the polymer is poly(lactic
acid).

There remains a need for cost-effective chemical recy-
cling of PLA and successful integration of the hydrolyzed
PLA with existing LA/PLA production processes.

There also remains a need to improve the yield of lactic
acid production, particularly from organic waste.

SUMMARY OF THE INVENTION

The present invention provides methods and systems for
highly efficient production of an enantiomerically pure lac-
tate salt, particularly an L-lactate salt, by combined recy-
cling of organic waste and PLA waste. More particularly, the
present invention integrates production of L-lactate mono-
mers by lactic acid fermentation of organic waste with
chemical hydrolysis of PLA to its constituting monomers (L-
and optionally D-lactate monomers). As disclosed herein,
L-lactate monomers produced by fermentation and lactate
monomers produced by chemical hydrolysis of PLA are
combined and purified together in a single downstream
purification and recovery process to obtain a pure L-lactate
salt. In some embodiments, the lactate monomers resulting
from PLA hydrolysis are combined with L-lactate mono-
mers produced by fermentation after the fermentation is
completed. Alternatively, lactate monomers produced by
PLA hydrolysis are supplemented to a lactic acid production
reactor in which L-lactate monomers are produced by fer-
mentation of organic waste, and subsequently the supplemented lactate monomers and newly produced L-lactate monomers are subjected to a single purification process to obtain a pure L-lactate salt. The purified L-lactate salt can then be acidified into L-lactic acid and used in the production of new PLA.

As disclosed herein, lactic acid fermentation is carried out in the presence of an alkaline compound that adjusts the pH during fermentation, resulting in a fermentation broth comprising L-lactate monomers and a counterion. The PLA hydrolysis is carried out using a metal oxide or a hydroxide, resulting in a hydrolysis slurry comprising lactate monomers (L- and optionally D-) and a counterion. The alkaline compound used during fermentation and the metal oxide or the hydroxide used for PLA hydrolysis according to the present invention produce L-lactate monomers and a counterion which may be the same or different with each possibility representing a separate embodiment. When using the same counterion, the L-lactate monomers and the counterions can be combined and purified together to obtain a pure lactate salt. When using a different counterion, at least one of the counterions can be exchanged thereby resulting in the same counterion which together with the L-lactate monomers can be subjected to subsequent combined purification. In some embodiments, the alkaline compound used during fermentation and the metal oxide or the hydroxide used for PLA hydrolysis are the same compound, namely, the same compound is used for both PLA hydrolysis and pH adjustment in the fermenter. For example, magnesium hydroxide can be used both as a hydroxide for PLA hydrolysis and as an alkaline compound for pH adjustment during fermentation, resulting in lactate monomers and magnesium ions in both the hydrolysis slurry and the fermentation broth, which can be recovered as magnesium lactate. In other embodiments, the compounds are different, but produce the same counterion. For example, magnesium hydroxide can be used as a hydroxide for PLA hydrolysis, and magnesium carbonate can be used as an alkaline compound for pH adjustment during fermentation, resulting in lactate monomers and magnesium ions in both the hydrolysis slurry and the fermentation broth, which can be recovered as magnesium lactate. In yet other embodiments, the compounds are different, but one of the counterions is exchanged to produce the same counterion as the other for subsequent purification. For example, sodium hydroxide can be used as a hydroxide for PLA hydrolysis, and magnesium hydroxide can be used as an alkaline compound for pH adjustment during fermentation. The sodium ions in the hydrolysis slurry can then be exchanged with magnesium ions thereby resulting in lactate monomers and magnesium ions in both the hydrolysis slurry and the fermentation broth, which can be recovered as magnesium lactate salt. In further embodiments, both counterions are exchanged to produce the same counterion for subsequent purification.

The present invention advantageously integrates the products of two processes, namely, i) lactate hydrolyzed from PLA and ii) lactate produced via fermentation of organic waste, into a single downstream purification process for recovering an L-lactate salt, thus saving both capital expenditure (CAPEX) and operational expenditure (OPEX).

In addition, the present invention improves the yield of L-lactic acid production from organic waste. Organic waste such as mixed food waste is characterized by high variability in terms of carbohydrate content, and its composition varies from batch to batch where some batches may be rich in carbohydrates compared to others that have a low carbohydrate content. Thus, lactic acid fermentation processes based on organic waste may result in varied yields from batch to batch, and in certain instances a very low yield of lactic acid is obtained. The integration of lactate hydrolyzed from PLA and lactate produced via fermentation of organic waste increases the amount of lactic acid that is obtained per fermentation cycle, thus improving the yield and facilitating reproducibility of lactic acid fermentation processes.

The systems and methods of the present invention therefore provide recycling of PLA and organic waste which is cost-effective and improves the yield of L-lactic acid production.

According to a first aspect, there is provided a method for producing an L-lactate salt from a combined recycling of polylactic acid (PLA) and organic waste, the method comprising the steps of:

(a) hydrolyzing PLA waste with a metal oxide or a hydroxide to obtain a PLA hydrolysis slurry comprising L-lactate monomers and a first counterion;

(b) fermenting organic waste with a lactic acid-producing microorganism in a fermenter in the presence of an alkaline compound to obtain a fermentation broth comprising L-lactate monomers and a second counterion, wherein the first and second counterions are the same; or wherein at least one of the first and second counterions is subjected to ion exchange thereby obtaining a first and second counterions which are the same;

(c) optionally contacting the PLA hydrolysis slurry of step (a), the fermentation broth of step (b), or a mixture comprising the PLA hydrolysis slurry of step (a) and the fermentation broth of step (b) with a D-lactic acid degrading enzyme or a D-lactic acid-utilizing microorganism to eliminate D-lactate monomers thereby obtaining L-lactate monomers; and (d) purifying a mixture comprising the PLA hydrolysis slurry of step (a) and the fermentation broth of step (b) or the L-lactate monomers of step (c) thereby obtaining an L-lactate salt.

In one embodiment, step (a) and step (b) are performed in any order or simultaneously, with each possibility representing a separate embodiment.

In some embodiments, the PLA hydrolysis slurry is gradually added to the lactic acid fermenter of step (b) during the fermentation. In accordance with these embodiments, the mixture comprising the PLA hydrolysis slurry of step (a) and the fermentation broth of step (b) is obtained by gradually adding the PLA hydrolysis slurry to the lactic acid fermenter during fermentation. In some embodiments, where the PLA hydrolysis slurry is added to the lactic acid fermenter of step (b), step (a) may comprise the metal oxide or the hydroxide in excess thereby obviating the need to add the alkaline compound to the lactic acid fermenter in step (b) for pH adjustment during fermentation.

Advantageously, the integration of the L-lactate monomers produced by lactic acid fermentation with the L-lactate monomers resulting from PLA hydrolysis into a single downstream purification process to obtain a purified L-lactate salt increases the overall yield of L-lactate production, which is particularly beneficial for organic wastes with a low carbohydrate content that cannot reach high titers of lactic acid. In one embodiment, the overall yield of L-lactate production is increased by 10% or more. In another embodiment, the overall yield of L-lactate production is increased by 50% or more. In yet another embodiment, the overall yield of L-lactate production is increased by 100% or more.

In certain embodiments, the lactate salt is magnesium L-lactate. In particular embodiments, the lactate salt is crystalline magnesium L-lactate. In specific embodiments, the lactate salt is crystalline magnesium L-lactate dihydrate.

In some embodiments, the metal oxide or hydroxide of step (a) and the alkaline compound of step (b) are the same compound.

In various embodiments, the alkaline compound of step (b) is a metal oxide, a carbonate or a hydroxide. Each possibility represents a separate embodiment.

In certain embodiments, the metal oxide comprises at least one of MgO, CaO and a mixture or combination thereof. Each possibility represents a separate embodiment.

In other embodiments, the carbonate comprises at least one of $CaCO_3$, $MgCO_3$ and a mixture or combination thereof. Each possibility represents a separate embodiment.

In certain embodiments, the hydroxide comprises at least one of NaOH, KOH, $NH_4OH$, $Ca(OH)_2$, $Mg(OH)_2$ and a mixture or combination thereof. Each possibility represents a separate embodiment.

In one particular embodiment, the hydroxide of step (a) is NaOH and the alkaline compound of step (b) is $Mg(OH)_2$. In another particular embodiment, the hydroxide of step (a) and the alkaline compound of step (b) are $Mg(OH)_2$.

In various embodiments, the hydrolysis in step (a) is performed at elevated temperatures in the range of about 50° C. to about 90° C., for example, temperatures in the range of about 60° C. to about 90° C., about 70° C. to about 90° C., about 50° C. to about 80° C., and about 50° C. to about 75° C., including each value within the specified ranges. Each possibility represents a separate embodiment.

In further embodiments, the hydrolysis in step (a) is performed for a period of time in the range of about 1 to about 12 hours, including each value within the specified range. In other embodiments, the hydrolysis in step (a) is performed for a period of time in the range of about 12 to about 36 hours, including each value within the specified range.

In additional embodiments, step (a) comprises hydrolyzing PLA waste with $Mg(OH)_2$ at a concentration of between about 5 to about 15 wt. % to obtain a PLA hydrolysis slurry comprising L-lactate monomers and a magnesium ion.

In other embodiments, the hydrolysis in step (a) results in L-lactate monomers and a first counterion in crystalline form. In yet other embodiments, the fermentation in step (b) results in L-lactate monomers and a second counterion in crystalline form.

In additional embodiments, the method for producing an L-lactate salt further comprises pretreatment of the PLA waste prior to step (a). In specific embodiments, pretreatment comprises a mechanical pretreatment selected from the group consisting of grinding, chipping, shredding, milling, and a combination thereof. Each possibility represents a separate embodiment. In other specific embodiments, pretreatment comprises extrusion pretreatment.

In further embodiments, the method for producing an L-lactate salt further comprises subjecting the PLA hydrolysis slurry obtained in step (a) to solid-liquid separation. It is contemplated that the solid-liquid separation provides the removal of unhydrolyzed PLA waste or impurities such as other polymers, inert materials and/or food waste from the slurry.

PLA waste according to the present invention may include non-PLA impurities and contaminants. In some embodiments, the PLA waste is sorted prior to step (a) to increase the amount of PLA in said waste relative to non-PLA impurities and contaminants. Advantageously, PLA recycling according to the present invention is insensitive to impurities and contaminants present in the PLA waste, including contaminants that cannot be sorted successfully. As disclosed herein, the PLA waste following the alkaline hydrolysis is integrated into a downstream purification process of a lactic acid fermentation broth, the downstream purification process simultaneously eliminates contaminants originating from both the organic waste that was used as the substrate for fermentation and the PLA waste.

In certain embodiments, the PLA waste comprises both poly L-lactic acid (PLLA) and poly D-lactic acid (PDLA).

In some embodiments, the organic waste comprises endogenous D-lactic acid, L-lactic acid or a combination thereof. Each possibility represents a separate embodiment.

In certain embodiments, where D-lactic acid is formed and/or present, the PLA hydrolysis slurry of step (a), the fermentation broth of step (b) or a mixture comprising the PLA hydrolysis slurry of step (a) and the fermentation broth of step (b) are contacted with a D-lactic acid degrading enzyme or a D-lactic acid-utilizing microorganism to eliminate D-lactate monomers thereby obtaining L-lactate monomers. In particular embodiments, the D-lactic acid degrading enzyme in step (c) is a D-lactate oxidase.

In some embodiments, the organic waste is selected from the group consisting of food waste, municipal waste, agricultural waste, plant material and a mixture or combination thereof. Each possibility represents a separate embodiment.

In other embodiments, the obtained L-lactate salt is purified by at least one of crystallization, recrystallization, distillation, partitioning, silica gel chromatography, preparative HPLC, and combinations thereof. Each possibility represents a separate embodiment.

In further embodiments, the obtained L-lactate salt is acidified to form L-lactic acid by at least one of hydrochloric acid, hydrobromic acid, phosphoric acid, sulfuric acid, and combinations thereof. Each possibility represents a separate embodiment. In particular embodiments, the L-lactic acid is used for subsequent polylactic acid formation.

According to a second aspect, there is provided a method for producing magnesium L-lactate salt by recycling of polylactic acid (PLA) waste, the method comprising the steps of:

(a) hydrolyzing PLA waste with a base selected from sodium, potassium and ammonium hydroxide to obtain a PLA hydrolysis slurry comprising L-lactate monomers and a counterion selected from sodium, potassium and ammonium;

(b) optionally performing at least one of neutralizing the PLA hydrolysis slurry with an acid and removing unhydrolyzed PLA waste; and (c) adding a magnesium salt to the PLA hydrolysis slurry of step (a) or (b) to thereby precipitate magnesium L-lactate salt.

In some embodiments, the base is sodium hydroxide.

In other embodiments, the hydrolysis in step (a) is performed at elevated temperatures in the range of about 50° C. to about 90° C., for example, temperatures in the range of about 60° C. to about 90° C., about 70° C. to about 90° C., about 50° C. to about 80° C., and about 50° C. to about 75° C., including each value within the specified ranges. Each possibility represents a separate embodiment.

In yet other embodiments, the hydrolysis in step (a) is performed for a period of time in the range of about 1 to about 24 hours, including each value within the specified range. In other embodiments, the hydrolysis in step (a) is performed for a period of time in the range of about 1 to about 12 hours, including each value within the specified range.

In certain embodiments, the base is in excess of the PLA waste. In alternative embodiments, the PLA waste is in excess of the base.

In further embodiments, step (b) is performed and the acid is selected from hydrochloric acid, hydrobromic acid, phosphoric acid, sulfuric acid, and combinations thereof. Each possibility represents a separate embodiment. In one embodiment, step (b) is performed and the acid is sulfuric acid.

In various embodiments, step (b) is performed and removing unhydrolyzed PLA waste comprises solid-liquid separation.

In additional embodiments, the magnesium salt in step (c) is added in solid form. In alternative embodiments, the magnesium salt in step (c) is added as an aqueous solution. In further embodiments, the magnesium salt in step (c) is gradually added. In particular embodiments, the magnesium salt in step (c) is magnesium sulfate.

In additional embodiments, the obtained magnesium L-lactate salt is further subjected to subsequent purification. In other embodiments, the magnesium L-lactate salt is combined with magnesium L-lactate salt derived from fermentation of organic waste followed by subsequent purification.

Other objects, features and advantages of the present invention will become clear from the following description, examples and drawings.

DETAILED DESCRIPTION OF THE INVENTION

Figure 1:
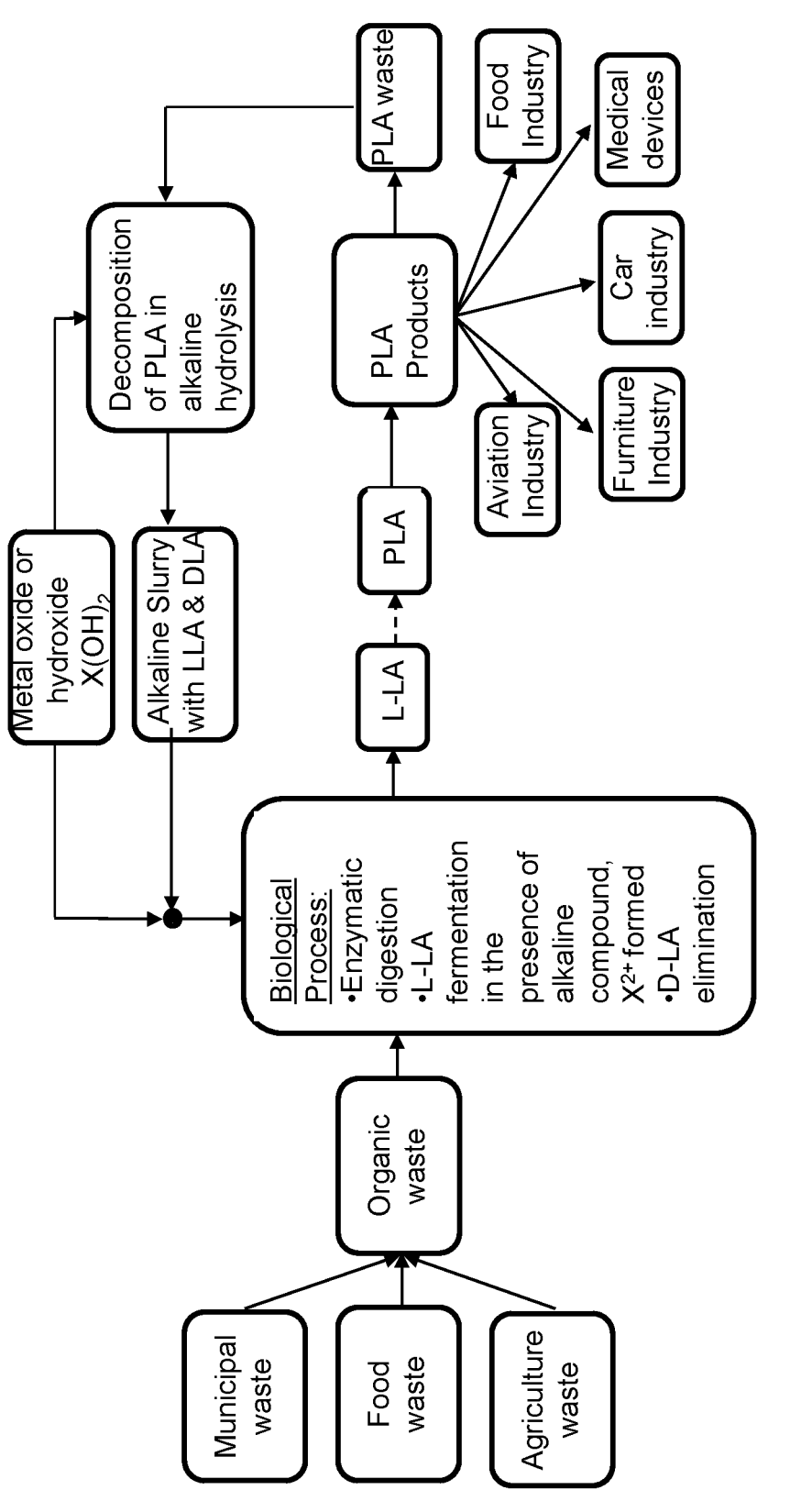
FIG. 1. Schematic illustration of a combined lactic acid production and PLA recycling according to certain embodiments of the present invention.

The present invention provides methods and systems for combined lactic acid fermentation and polylactic acid (PLA) recycling, to obtain enantiomerically pure L-lactate salts at high yields.

The provided systems and methods readily induce degradation of PLA waste back into its constituting monomers—lactic acid (LA), and efficiently recycle the LA monomers into PLA production processes. Even though PLA is considered a biodegradable bioplastic, its rate of hydrolysis is relatively low in aqueous or alcoholic solutions. In addition, PLA degradation that occurs in the "open environment" can be considered as waste, since the lactic acid that is produced is not being reused. The present invention not only provides accelerated degradation of PLA waste but also provides cost-effective sustainable recycling of PLA, as the LA monomers obtained from the hydrolysis are provided in the form of a lactate salt, which is then combined and integrated into downstream purification processing of lactic acid fermentation broths derived from organic waste.

As used herein, the term "lactic acid" refers to the hydroxycarboxylic acid with the chemical formula $CH_3CH(OH)CO_2H$. The terms lactic acid or lactate (unprotonated lactic acid) can refer to the stereoisomers of lactic acid: L-lactic acid/L-lactate, D-lactic acid/D-lactate, or to a combination thereof.

For most industrial applications, L-lactic acid monomers with high purity are required in order to produce PLA with suitable properties. Thus, the methods and systems of the present invention are directed, in particular, to processes for the production of L-lactate salts at high yields, which can then be converted to L-lactic acid suitable for reuse.

In particular, the present invention provides the combined recycling of PLA waste and organic waste. According to the principles provided herein, PLA recycling is performed via hydrolysis of PLA waste, and organic waste recycling is performed via lactic acid fermentation, wherein both processes resulting in lactate monomers and the same counterion. It is to be understood, that when the resulting counterions are different, at least one of the hydrolysis or fermentation products can be subjected to an ion exchange processing step to obtain the same counterion. The products obtained from hydrolysis of PLA and lactic acid fermentation are combined and processed together to obtain a pure lactate salt, preferably an L-lactate salt at high yields. The L-lactate salt can then be purified to obtain highly purified L-lactate salt with improved yield. In some embodiments, the recovered L-lactate salt can be converted into lactic acid and used for the production of new PLA.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Referring now to the drawings, FIG. 1 provides a general overview of a combined L-lactic acid production and PLA recycling according to embodiments of the present invention. Organic waste such as municipal waste, food waste and agricultural waste serves as the substrate for L-lactic acid fermentation by L-lactic acid-producing microorganisms. The organic waste undergoes a biological process resulting in the production of L-lactic acid. The biological process includes enzymatic digestion of the waste using polysaccharide-degrading enzymes (e.g. amylase, cellulase) in order to degrade polysaccharides present in the waste and release soluble reducing sugars suitable for fermentation. The biological process further includes L-lactic acid fermentation by an L-lactic acid-producing microorganism. Due to the formation of L-lactic acid, endogenous lowering of the pH occurs. Thus, the fermentation process is carried out in the presence of an alkaline compound to adjust the pH during fermentation. The alkaline compound neutralizes the pH resulting in the formation of a counterion, represented in FIG. 1 as $X^{2+}$ for illustration purposes. It is to be understood that the alkaline compound that is used may comprise a monovalent cation thereby resulting in a monovalent counterion in the fermentation broth. The enzymatic digestion and lactic acid fermentation may be carried out simultaneously. Alternatively, enzymatic digestion may be carried out before lactic acid fermentation, in the same reactor in which fermentation is carried out or in a different reactor. Each possibility represents a separate embodiment. The biological process and/or the PLA hydrolysis may further include D-lactate elimination. D-lactate elimination may be carried out at the end of fermentation to eliminate D-lactate that was present in the organic waste, at the end of PLA hydrolysis to eliminate D-lactate that was present in the PLA waste or generated during hydrolysis, or after mixing the fermentation broth with the PLA hydrolysis slurry. Each possibility represents a separate embodiment. D-lactate elimination may be carried out in the same reactors in which fermentation and hydrolysis were carried out or in a different reactor. Each possibility represents a separate embodiment.

PLA waste according to the present invention includes any discarded PLA product for example discarded PLA separated from municipal solid waste (=MSW) or industrial/commercial rejects/scraps remaining from the production of PLA products. For example, PLA waste products may be obtained from the food industry, medical devices, car industry, furniture industry, and aviation industry. Each possibility represents a separate embodiment. PLA waste undergoes decomposition via alkaline hydrolysis. A metal oxide or a hydroxide, represented in FIG. 1 as $X(OH)_2$ for illustration purposes, is mixed with PLA waste. It is to be understood that the metal oxide or the hydroxide that is used may comprise a monovalent cation thereby resulting in a monovalent counterion in the hydrolysis slurry together with L-lactate monomers. Where the PLA waste includes PLLA and PDLA, the hydrolysis slurry may further contain D-lactate monomers. In some embodiments, the hydrolysis slurry is mixed with the lactic acid fermentation broth after fermentation is completed. In other embodiments, the hydrolysis slurry comprises an excess of the metal oxide or hydroxide thereby exerting an alkaline pH, and is gradually added to the lactic acid fermentation process during fermentation. The alkaline slurry neutralizes the pH of the fermentation broth thereby obviating the need to add a pH adjusting agent separately. A mixture of the PLA hydrolysis slurry and the fermentation broth is then processed to obtain purified L-LA salt. L-LA salt can then by reacidified and polymerized to form PLA useful in the production of PLA products, thereby completing a cycle of PLA decomposition and synthesis, and recycling organic waste to lactic acid.

Figure 2:
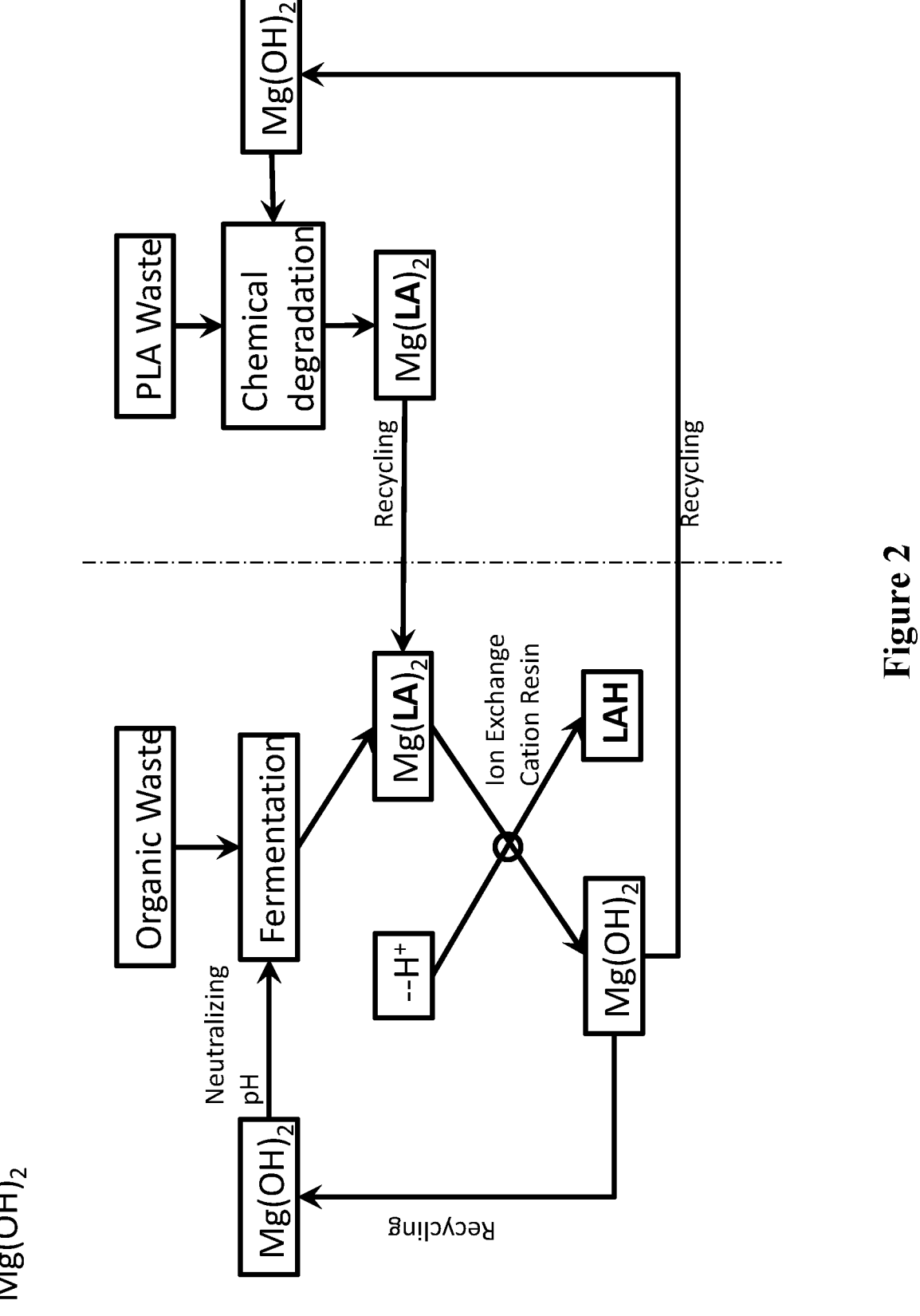
FIG. 2. Schematic illustration of a combined lactic acid production and PLA recycling according to additional embodiments of the present invention, in which $Mg(OH)_2$ is used as a PLA alkaline hydrolysis agent and as a pH adjusting alkaline compound in lactic acid fermentation.

FIG. 2 illustrates a combined process according to some embodiments of the present invention, in which $Mg(OH)_2$ is used both as the PLA alkaline hydrolysis agent and as the pH adjusting alkaline compound in lactic acid fermentation. PLA waste undergoes chemical degradation using $Mg(OH)_2$, to obtain $Mg(LA)_2$. Organic waste undergoes fermentation by an L-lactic acid-producing microorganism in the presence of $Mg(OH)_2$ for pH neutralization, resulting in $Mg(L-LA)_2$. $Mg(LA)_2$ obtained from PLA hydrolysis and $Mg(LA)_2$ produced by fermentation are combined and subjected to acidification to obtain L-lactic acid (LAH) and $Mg(OH)_2$. The LAH can be used in the synthesis of new PLA. The $Mg(OH)_2$ can be re-used for pH adjustment and/or PLA hydrolysis in further lactic acid fermentation and PLA hydrolysis processes.

Figure 3:
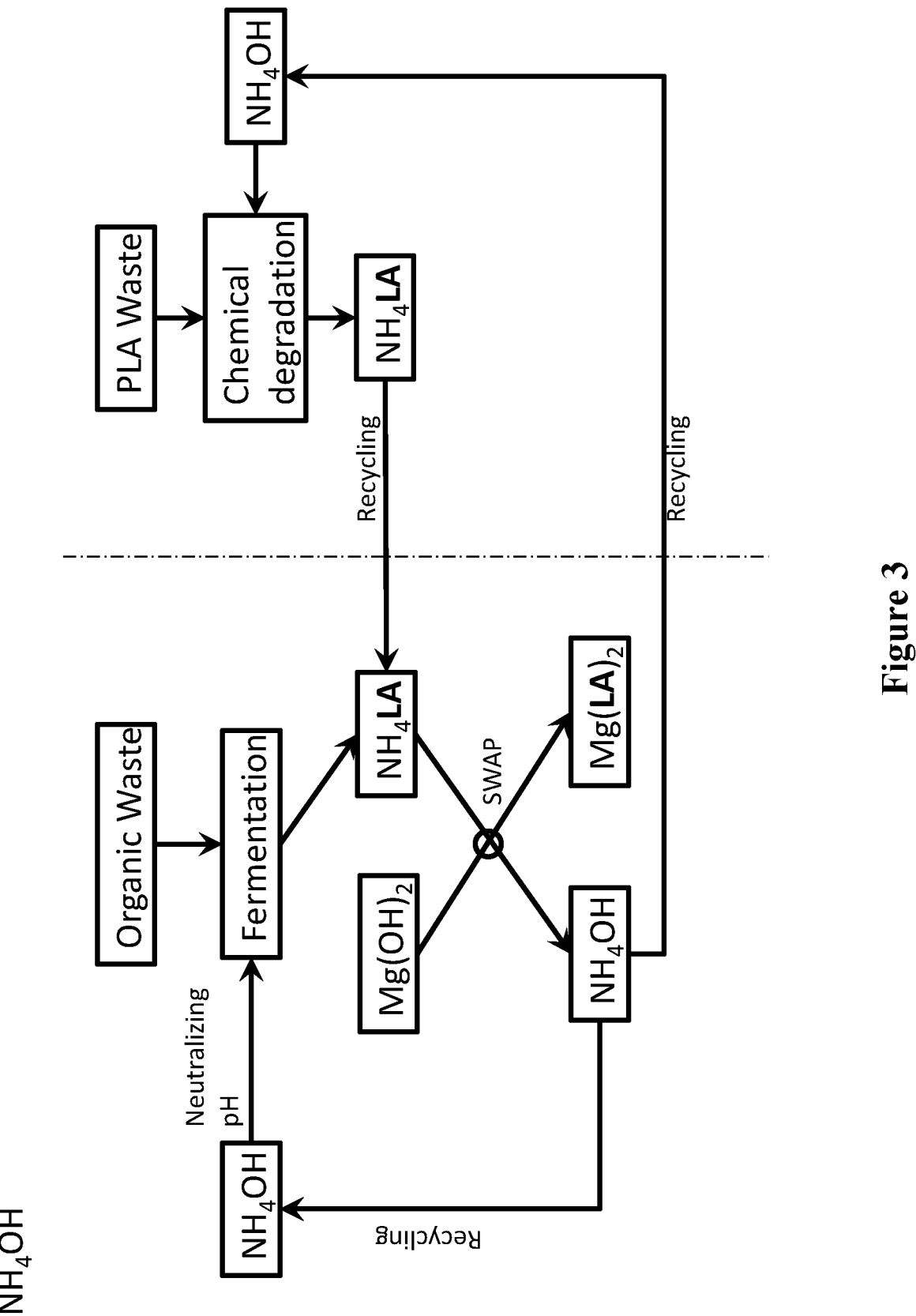
FIG. 3. Schematic illustration of a combined lactic acid production and PLA recycling according to additional embodiments of the present invention, in which $NH_4OH$ is used as a PLA alkaline hydrolysis agent and as a pH adjusting alkaline compound in lactic acid fermentation, and in which ion exchange is carried out in order to obtain $Mg(LA)_2$ that can be recovered and purified.

FIG. 3 illustrates a combined process according to additional embodiments of the present invention, in which $NH_4OH$ is used as the PLA alkaline hydrolysis agent and as the pH adjusting alkaline compound in lactic acid fermentation, and in which ion exchange is carried out in order to obtain $Mg(LA)_2$ that can be recovered and purified. PLA waste undergoes chemical degradation using $NH_4OH$, to obtain $NH_4LA$. Organic waste undergoes fermentation by an L-lactic acid-producing microorganism in the presence of $NH_4OH$ for pH neutralization, resulting in $NH_4(L-LA)$. $NH_4LA$ obtained from PLA hydrolysis and $NH_4LA$ produced by fermentation are combined and subjected to ion exchange with $Mg(OH)_2$, to obtain $Mg(LA)_2$ and $NH_4OH$. The $Mg(LA)_2$ can be recovered, purified and acidified to obtain LAH, that can be used in the synthesis of new PLA. The $NH_4OH$ can be re-used for pH adjustment and/or PLA hydrolysis in further lactic acid fermentation and PLA hydrolysis processes. Alternatively, $NH_4OH$ can be discarded by evaporation of ammonia gas.

According to certain exemplary embodiments of the present invention, a process is performed using NaOH as the PLA alkaline hydrolysis agent and $Mg(OH)_2$ as the pH adjusting alkaline compound in lactic acid fermentation. Ion exchange is carried out to the hydrolysis slurry to obtain $Mg(LA)_2$ which is then combined with the $Mg(LA)_2$ of the fermentation broth. The $Mg(LA)_2$ can be recovered, purified and acidified to obtain LAH for subsequent PLA formation.

According to the principles of the present invention, the counterion present in the PLA hydrolysis (first counterion) and/or the counterion present in the fermentation broth (second counterion) are either the same counterion or are exchanged to the same counterion. Even in instances where the same counterion is produced during hydrolysis and fermentation, the present invention encompasses embodiments whereby the first and second counterions are exchanged to result in a desirable lactate salt. Ion exchange can be performed as is known in the art, for example by using cation exchange resins. Cation exchange resins are negatively charged polymers that can freely exchange associated cations based on differences in the selectivities of the cations. Suitable cation exchange resins within the scope of the present invention include, but are not limited to, those obtained from commercial sources such as DOWEX™ cation exchange resins. In other embodiments, ion exchange can be performed by neutralizing the lactate salt using a suitable acid including, but not limited to, hydrochloric acid, hydrobromic acid, phosphoric acid, sulfuric acid, and combinations thereof, followed by exposing the resulting lactic acid to a base or salt comprising the desired counterion. Suitable bases include, but are not limited to, sodium, potassium, magnesium and calcium hydroxides. Each possibility represents a separate embodiment. Currently preferred is the use of magnesium salts selected from $MgCl_2$, $MgCO_3$, $MgSO_4$, $Mg_3(PO_4)_2$ and the like, to result in magnesium lactate. Each possibility represents a separate embodiment. Further embodiments encompassed by the present invention include the use of PLA in excess of the metal oxide or the hydroxide. In accordance with these embodiments, following PLA decomposition, the excess PLA is separated from the hydrolysis slurry which is then subjected to ion exchange using a salt as described hereinabove. Advantageously, when using PLA in excess, no neutralizing of the lactate salt by an acid following hydrolysis is required.

PLA waste according to the principles of the present invention may be sorted before being used in the method of the present invention in order to increase the relative amount of PLA in the waste compared to non-PLA materials. Generally, there are three types of PLA polymers: homopolymers, copolymers, and stereocomplexes. Homopolymers are composed of 100% L-lactic acid (PLLA) or 100% D-lactic acid (PDLA). The common commercial copolymer of PLA is PDLLA (Poly (D-L-)Lactic Acid), predominantly composed of L-lactic acid, with small amounts of D-lactic acid. Stereocomplex PLA (sc-PLA) is also available, which consists of PLLA and PDLA chains, where PLLA and PDLA chains are packed together to form a super structure with improved thermal and mechanical properties over PLLA.

Thus, most commercial PLA includes L-lactic acid as the major constituent but also D-lactic acid, and therefore both isoforms will be present in the hydrolysis slurry following chemical hydrolysis of the PLA. In addition, racemization during hydrolysis may contribute to unknown and uncontrolled amounts of D-lactic acid.

Without being bound by any theory or mechanism of action, the hydrolysis of PLA typically occurs via surface erosion in which the ester groups are hydrolyzed mainly on the surface of discarded PLA, proceeding via an erosion front or a plurality of erosion fronts to the bulk. Surface hydrolysis typically occurs when the kinetics of bond hydrolysis is more rapid than water diffusion. Accordingly, it is desirable to increase the surface area thereby accelerating the hydrolysis process. Suitable manners for increasing surface area include mechanical pretreatment such as, but not limited to, grinding, chipping, shredding, and milling. Each possibility represents a separate embodiment. In further embodiments, surface area can be increased using enzymatic hydrolysis as a pretreatment to chemical hydrolysis. In certain aspects and embodiments, the surface area of the discarded PLA may be increased using extrusion pretreatment, optionally accompanied by the alkaline hydrolysis. Extrusion pretreatment utilizes a combination of heat, compression forces, and shear forces that lead to physical disruption and chemical modifications of the material passing through the extruder. The alkaline hydrolysis may be combined with the extrusion in order to improve the efficiency of the process. The extruder that may be used includes, but is not limited to, a single screw extruder, a twin screw extruder including co-rotating, counter-rotating, intermeshing, and non-intermeshing extruders, a multiple screw extruder, a ram extruder which utilizes a heated cylinder and a piston for extruding the feed, a gear-pump extruder which utilizes a heated gear pump, and a conveyer extruder. Each possibility represents a separate embodiment.

It is to be understood that the aforementioned pretreatments (e.g. extrusion) may also be utilized as part of the process of the present invention sequentially following one or more steps of the process, simultaneously with one or more steps of the process, or a combination thereof. Each possibility represents a separate embodiment. Embodiments in which the entire process is accompanied by one or more of the aforementioned pretreatments are contemplated as well.

In some aspects and embodiments, the pretreated PLA is fed into an alkaline slurry comprising a metal oxide or a hydroxide for inducing alkaline hydrolysis. Suitable metal oxides within the scope of the present invention include, but are not limited to MgO, CaO, and a mixture of combination thereof. Each possibility represents a separate embodiment. Hydroxides suitable for use within the scope of the present invention include, but are not limited to, NaOH, KOH, $NH_4OH$, $Ca(OH)_2$, $Mg(OH)_2$, and a mixture or combination thereof. Each possibility represents a separate embodiment. Currently preferred is the use of magnesium hydroxide thereby resulting in magnesium lactate. Where magnesium hydroxide is used for hydrolysis, it is typically present in a concentration of about 2 to about 15 wt. % including each value within the specified range. Additionally preferred embodiments include the use of sodium hydroxide for hydrolysis thereby resulting in sodium lactate which can then be subjected to ion exchange using e.g. $MgCl_2$, $MgCO_3$, $MgSO_4$, $Mg_3(PO_4)_2$, $Mg(OH)_2$ and the like to result in magnesium lactate. Where sodium hydroxide is used for hydrolysis, it is typically present in a concentration of 1N to about 10N, including each value within the specified range.

Optionally, at least one additive suitable for accelerating PLA hydrolysis can also be used together with the metal oxide or hydroxide. Additives that may be used for accelerating PLA hydrolysis include, but are not limited to, a phase transfer catalyst such as a quaternary ammonium salt selected from benzalkonium chloride, benzyltriethylammonium chloride, methyltricaprylammonium chloride, methyltributylammonium chloride, and methyltrioctylammonium chloride, with each possibility representing a separate embodiment; or a quaternary phosphonium salt selected from tetrabutylphosphonium bromide, tetraphenylphosphonium chloride, tetraphenylphosphonium bromide, and hexadecyltributylphosphonium bromide, with each possibility representing a separate embodiment. Additional additives that may be used for accelerating PLA hydrolysis include enzymatic catalysts e.g. lipases.

The step of hydrolyzing PLA waste may further involve the use of thermohydrolysis in place of or in addition to the alkaline chemical hydrolysis detailed above. Typically, thermohydrolysis is performed at elevated temperatures in the range of about 50° C. to about 90° C., including each value within the specified range. Typically, temperatures in the range of about 60° C. to about 90° C., about 70° C. to about 90° C., about 50° C. to about 80° C., about 50° C. to about 75° C., including each value within the specified ranges can be used. Each possibility represents a separate embodiment. The duration of thermohydrolysis can be performed for period of time in the range of about 1 to about 36 hours, including each value within the specified range. Exemplary durations include, but are not limited to, about 1 to about 12 hours, about 12 hours to about 36 hours and any duration therebetween. Typically, thermohydrolysis is performed for about 1 hour, about 2 hours, about 4 hours, about 6 hours, about 10 hours, about 12 hours, about 14 hours, about 16 hours, about 18 hours, about 20 hours, about 22 hours, or about 24 hours. Each possibility represents a separate embodiment.

In case where there are particles of PLA waste which have failed to be hydrolyzed, they may be separated from the hydrolysis slurry, for example by solid-liquid separation techniques such as filtration or decantation. Each possibility represents a separate embodiment. In some embodiments, the lactate monomers in the form of a lactate salt are crystallized at the end of the hydrolysis step. For example, a PLA hydrolysis slurry may be subjected to evaporation and/or cooling to obtain crystals of lactate salts. The crystals can be collected and integrated into the lactic acid production process as described herein.

According to the principles of the present invention, further provided herein is a method for producing magnesium L-lactate salt by recycling of polylactic acid (PLA) waste. The method advantageously provides PLA chemical hydrolysis at lower temperatures and shorter time durations (for example, less than 12 hours, less than 10 hours, or even less than 5 hours) and further affords decomposition of denser and more compact PLA waste. PLA waste (which may be pretreated as described herein) is hydrolyzed using a base selected from sodium, potassium and ammonium hydroxide to obtain a PLA hydrolysis slurry comprising L-lactate monomers and a counterion selected from sodium, potassium and ammonium. Each possibility represents a separate embodiment. Currently preferred is the use of sodium hydroxide as a base thereby obtaining a PLA hydrolysis slurry comprising L-lactate and sodium ions. Hydrolysis is typically performed at elevated temperatures in the range of about 50° C. to about 90° C. for a duration of about 1 to about 36 hours, preferably between about 1 to about 24 hours, including each value within the specified ranges. Exemplary temperatures ranges include, but are not limited to, about 60° C. to about 90° C., about 70° C. to about 90° C., about 50° C. to about 80° C., and about 50° C. to about 75° C., including each value within the specified ranges. Each possibility represents a separate embodiment. Exemplary durations of hydrolysis include, but are not limited to, about 1 to about 5 hours, about 1 to about 10 hours, about 1 to about 12 hours, about 1 to about 24 hours, about 12 to about 24 hours and about 12 to about 36 hours, including each value within the specified ranges. In some embodiments, the base is in excess of the PLA waste thereby resulting in a PLA slurry at pH range of about 10 to about 14, including each value within the specified range. In alternative embodiments, the PLA waste is in excess of the base thereby resulting in a PLA slurry at pH range of about 7 to about 10, including each value within the specified range. The hydrolysis slurry may then be subjected to neutralization using an acid such as, but not limited to, hydrochloric acid, hydrobromic acid, phosphoric acid, sulfuric acid, and combinations thereof. Each possibility represents a separate embodiment. Additionally or alternatively, the hydrolysis slurry may be subjected to removal of unhydrolyzed PLA for example by solid-liquid separation techniques using e.g. filtration or decantation. Each possibility represents a separate embodiment.

Magnesium salt is then added to induce precipitation of magnesium L-lactate. The magnesium salt can be added in solid form or as an aqueous solution. Each possibility represents a separate embodiment. Currently preferred is the addition of magnesium salt as an aqueous solution at a concentration ranging from about 50 to about 500 g/L, including each value within the specified range. In some embodiments, the magnesium salt aqueous solution is gradually added to the PLA slurry while mixing. Magnesium salts within the scope of the present invention include, but are not limited to, $MgCl_2$, $MgCO_3$, $MgSO_4$, $Mg_3(PO_4)_2$, $Mg(OH)_2$ and the like. Each possibility represents a separate embodiment. Currently preferred is the addition of magnesium sulfate (e.g. magnesium sulfate heptahydrate). The thus obtained magnesium L-lactate salt may further be subjected to downstream purification processes with or without magnesium L-lactate salt from a lactic acid fermentation.

The carbon source for lactic acid fermentation according to the present invention is derived from organic waste. Organic waste suitable for use according to certain embodiments of the present invention include, but are not limited to, food waste, organic fraction of municipal waste, agricultural waste, plant material, and a mixture or combination thereof. Each possibility represents a separate embodiment. Food waste in accordance with the present invention encompasses food waste of plant origin. Food waste in accordance with the present invention encompasses household food waste, commercial food waste, and industrial food waste. Each possibility represents a separate embodiment. The organic food waste may originate from vegetable and fruit residues, plants, cooked food, protein residues, slaughter waste, and combinations thereof. Each possibility represents a separate embodiment. Industrial organic food waste may include factory waste such as by products, factory rejects, market returns or trimmings of inedible food portions (such as peels). Commercial organic food waste may include waste from shopping malls, restaurants, supermarkets, etc. Plant material in accordance with the present invention encompasses agricultural waste and manmade products such as paper waste. Typically, organic waste comprises endogenous D-lactic acid, L-lactic acid or both L- and D-lactic acid, originating, for example, from natural fermentation processes, e.g., in dairy products.

Lactic acid fermentation is performed using a lactic acid-producing microorganism. "LA-producing microorganisms" as used herein refers to microorganisms that produce lactic acid as the major metabolic end product of carbohydrate fermentation. Currently preferred is the use of microorganisms which produce only L-lactic acid. The LA-producing microorganisms may produce only L-lactic acid naturally, or may be genetically modified to produce only L-lactic acid, for example by knocking out one or more enzymes involved in the synthesis of the undesired D-enantiomer. LA-producing microorganisms include various bacteria, including for example *Lactobacillus* species and *Bacillus* species, and fungi.

Fermentation is typically performed in the presence of an alkaline compound, such as a metal oxide, a carbonate or a hydroxide as detailed above. Suitable alkaline compounds include, but are not limited to, MgO, CaO, $CaCO_3$, $MgCO_3$, NaOH, KOH, $NH_4OH$, $Ca(OH)_2$, $Mg(OH)_2$, and a mixture or combination thereof. Each possibility represents a separate embodiment. The alkaline compound is added to adjust the pH of the fermentation broth to a desired value, typically in the range of 5 to 7, including each value within the specified range. The alkaline compound further results in the neutralization of the L-lactic acid to a lactate salt. During fermentation, the pH in the fermenter decreases due to the production of the lactic acid, which adversely affects the productivity of the lactic acid-producing microorganism. Adding bases such as magnesium-, sodium-, potassium-, or calcium-hydroxide adjusts the pH by neutralizing the lactic acid thereby resulting in the formation of a lactate salt. In embodiments in which the PLA hydrolysis slurry is added to the fermenter during fermentation, the PLA hydrolysis slurry may contain a metal oxide or a hydroxide in excess. The metal oxide or the hydroxide in excess adjusts the pH in the fermenter, thereby obviating the need for separate addition of an alkaline compound to adjust the pH during fermentation.

Additional advantage stemming from supplementing the fermentation broth with PLA hydrolysis slurry is an increase in the overall yield of L-lactate production, which is particularly beneficial for organic wastes with a low carbohydrate content. The overall yield of L-lactate production is typically increased by at least 10%, preferably by at least 30%, 40%, 50%, 60%, 70%, 80%, 90%, or even 100% or more. Each possibility represents a separate embodiment.

Typically, the fermenting is carried out under anaerobic or microaerophilic conditions, using batch, fed-batch, continuous or semi-continuous fermentation. Each possibility represents a separate embodiment of the present invention.

In batch fermentation, the carbon substrates and other components are loaded into the reactor, and when the fermentation is completed, the product is collected. Except for the alkaline compound discussed above for pH control, other ingredients are not added to the reaction before it is completed. The inoculum size is typically about 5-10% of the liquid volume in the reactor. The fermentation is kept at substantially constant temperature and pH, where the pH is maintained by adding the alkaline compound.

In fed-batch fermentation, the substrate is fed continuously or sequentially to the reactor without the removal of fermentation broth (i.e., the product(s) remain in the reactor until the end of the run). Common feeding methods include intermittent, constant, pulse-feeding, and exponential feeding. Each possibility represents a separate embodiment.

In continuous fermentation, the substrate is added to the reactor continuously at a fixed rate, and the fermentation products are taken out continuously.

In semi-continuous processes, a portion of the culture is withdrawn at intervals and fresh medium is added to the system. Repeated fed-batch culture, which can be maintained indefinitely, is also considered a semi-continuous process.

Lactic acid fermentation is typically carried out for about 1-4 days or any amount therebetween, for example, 1-2 days, or 2-4 days, or 3-4 days, including each value within the specified ranges.

After fermentation is completed, the broth may be clarified by centrifugation or passed through a filter press to separate solid residue from the fermented liquid. The filtrate may be concentrated, e.g. by using a rotary vacuum evaporator.

The fermentation broth according to the present invention may contain D-lactic acid originating from the organic waste. In addition, D-lactic acid may be present in the PLA hydrolysis slurry, either from degraded PLA or formed by racemization during hydrolysis. The D-LA is undesired in the production of L-LA for polymerization as it results in formation of more D,D-lactide and meso-lactide, which adversely impact the quality of the PLLA final product. Where D-LA is formed, the present invention advantageously eliminates it by employing a D-lactic acid degrading enzyme or a D-lactic acid utilizing microorganism to each of the fermentation broth or hydrolysis slurry alone, or to their combined mixture. Each possibility represents a separate embodiment.

Currently preferred is the use of a D-lactate oxidase as a D-lactic acid degrading enzyme. A D-lactate oxidase is an enzyme that catalyzes the oxidation of D-lactate to pyruvate and $H_2O_2$ using $O_2$ as an electron acceptor. The enzyme uses flavin adenine dinucleotide (FAD) as a co-factor for its catalytic activity. A D-lactate oxidase according to the present invention is typically a soluble D-lactate oxidase (rather than membrane-bound). Advantageously, the enzyme works directly in the fermentation broth to eliminate the D-lactic acid. In some embodiments, the D-lactate oxidase is from *Gluconobacter* sp. In some embodiments, the D-lactate oxidase is from *Gluconobacter oxydans* (see, for example, GenBank accession number: AAW61807). Elimination of D-lactate from fermentation broths derived from organic wastes using a D-lactate oxidase is described in WO 2020/208635 assigned to the Applicant of the present invention.

Suitable D-lactic acid-utilizing microorganisms within the scope of the present invention include, but are not limited to, an *Escherichia coli* lacking all three L-lactate dehydrogenases.

As used herein, "elimination", when referring to D-lactic acid/D-lactate, refers to reduction to residual amounts such that there is no interference with downstream processes of producing L-lactic acid and subsequently polymerization to poly(L-lactic acid) that is suitable for industrial applications. "Residual amounts" indicates less than 1% (w/w) D-lactate, and even more preferably less than 0.5% (w/w) D-lactate, out of the total lactate (L+D) in a treated mixture of a fermentation broth at the end of fermentation together with products of PLA hydrolysis. In some particular embodiments, elimination of D-lactate is reduction to less than 0.5% (w/w) D-lactic acid out of the total lactate in a treated mixture of a fermentation broth at the end of fermentation together with products of PLA hydrolysis.

According to further aspects and embodiments, the L-lactate monomers are further purified. The L-lactate monomers may be purified as L-lactate salts. Typically purification of L-lactate salts can be performed by at least one of crystallization, recrystallization, distillation, partitioning, silica gel chromatography, preparative HPLC, and combinations thereof. Each possibility represents a separate embodiment. Alternatively, a re-acidification step may be carried out in order to obtain crude L-lactic acid, followed by purification steps to obtain a purified L-lactic acid. Re-acidification can be performed as is known in the art, for example by using at least one of hydrochloric acid, hydrobromic acid, phosphoric acid, sulfuric acid, and combinations thereof. Each possibility represents a separate embodiment.

The purification processes may include distillation, extraction, electrodialysis, adsorption, ion-exchange, crystallization, and combinations of these methods. Several methods are reviewed, for example, in Ghaffar et al. (2014) *Journal of Radiation Research and Applied Sciences,* 7(2): 222-229; and López-Garzón et al. (2014) *Biotechnol Adv.,* 32(5): 873-904. Alternatively, recovery and conversion of lactic acid to lactide in a single step may be used (Dusselier et al. (2015) *Science,* 349(6243): 78-80).

In some particular embodiments of the present invention, the metal oxide or hydroxide that is used for PLA hydrolysis and the alkaline compound that is used for pH adjustment during fermentation produce a magnesium ion as the counterion. For example, in some embodiments, magnesium hydroxide ($Mg(OH)_2$) is used for PLA hydrolysis and also for pH adjustment during fermentation. In other embodiments, other cations (e.g. sodium or calcium ions) are used in the PLA hydrolysis and during fermentation which are exchanged to magnesium ions as described above. According to these embodiments, the PLA hydrolysis slurry comprises lactate monomers and $Mg^{2+}$, and the lactic acid fermentation broth comprises lactate monomers and $Mg^{2+}$, which can be recovered as magnesium lactate. Magnesium lactate can be obtained in a crystalline or amorphous form with each possibility representing a separate embodiment. Any solvate or polymorph of magnesium L-lactate can be recovered including, in particular, crystalline magnesium L-lactate dihydrate.

A particular downstream purification process for purifying magnesium lactate via crystallization is described in a co-pending patent application, WO 2020/110108, assigned to the Applicant of the present invention. The purification process can be applied to the mixture of the PLA hydrolysis slurry with the fermentation broth after treatment that eliminates D-lactate monomers where applicable. The purification process comprises the following steps:

providing a clarified mixture from which insoluble impurities have been removed, wherein the clarification can be performed to the fermentation broth prior to or following the step of mixing with the PLA hydrolysis slurry, the clarified mixture comprising magnesium lactate in a soluble form, the mixture being at a temperature between 45° C. to 75° C.;

concentrating the clarified mixture to a concentration of 150-220 g/L of lactate;

performing at least one cooling crystallization of the concentrated clarified mixture to obtain magnesium lactate crystals; and collecting the magnesium lactate crystals obtained.

In some embodiments, the mixture is provided at a temperature between 55° C. to 65° C.

The separation of insoluble impurities may include at least one technique selected from: filtration, centrifugation, flotation, sedimentation, flocculation and decantation. Each possibility represents a separate embodiment. For example, the separation of insoluble impurities can be carried out using centrifugation and microfiltration.

The concentration of the clarified mixture may be performed by evaporation, nanofiltration, reverse osmosis, or combinations thereof. In some embodiments, the clarified mixture is concentrated to a concentration of 160-220 g/L of lactate, for example, 170-220 g/L of lactate, 180-220 g/L of lactate, including each value within the specified ranges.

The at least one cooling crystallization may begin at a first temperature in the range of 50 to 75° C., including each value within the specified range. In some embodiments, the at least one cooling crystallization begins at a first temperature in the range of 50 to 70° C., including each value within the specified range. In additional embodiments, the at least one cooling crystallization begins at a first temperature in the range of 50 to 65° C., including each value within the specified range.

The at least one cooling crystallization step may end at a second temperature in the range of 10 to 1° C., including each value within the specified range. In some embodiments, the at least one cooling crystallization ends at a second temperature in the range of 6 to 2° C., including each value within the specified range.

The cooling rate of the at least one cooling crystallization may be in the range of 10 to 0.5° C./h, including each value within the specified range. In some embodiments, the cooling rate is in the range of 5 to 1° C./h, including each value within the specified range.

Before the cooling crystallization, the pH of the concentrated mixture may be adjusted to be in the range of 6 to 7.

The obtained magnesium lactate crystals may be separated from the remaining liquid by microfiltration or nanofiltration. The remaining liquid may undergo concentration, followed by at least one additional cooling crystallization, in order to obtain additional magnesium lactate crystals. Following their separation from the liquid, the magnesium lactate crystals may be washed with an aqueous solution or with an organic solvent such as ethanol and purified. Further processing of the magnesium lactate crystals may include at least one of extraction, microfiltration, nanofiltration, active carbon treatment, distillation, drying and grinding. Each possibility represents a separate embodiment.

As used herein and in the appended claims, the term "about" refers to ±10%. As used herein and in the appended claims, the singular forms "a", "an", and "the" include plural references unless the context clearly dictates otherwise. Thus, for example, reference to "an alkaline compound" includes a plurality of such compounds unless the context clearly dictates otherwise. It should be noted that the term "and" or the term "or" are generally employed in its sense including "and/or" unless the context clearly dictates otherwise.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Alkaline Thermohydrolysis of Thin-Film PLA Bags using Magnesium Hydroxide

The following experiment tested hydrolysis of thin-film PLA bags from post-consumer waste using magnesium hydroxide.

Substrate Preparation

PLA bags were manually cut with scissors into small rectangle-shaped pieces with dimensions of about 3×5 cm. Each cut piece of PLA bag weighed roughly around 100-200 mg.

Experimental Design

In order to evaluate the amount of $Mg(OH)_2$ that is needed to achieve full degradation of PLA products, 5 g of cut pieces of PLA bags were subjected to hydrolysis in 150 mL DW using 0 (as control), 1, 2.5, 5, 10 and 15 wt. % of $Mg(OH)_2$. The reactions were carried out at 90° C. for 24 h.

Procedure:

All reactions were carried out inside a 250 mL round-bottomed flask equipped with a large oval-shaped magnetic stirring bar. $Mg(OH)_2$ was added to each flask using a powder funnel to form a milky suspension. The flasks were placed inside an oil bath and heated to 90° C. for 24 h with stirring. Next, the suspension from each flask was vacuum filtered using a 90 mm Buchner funnel equipped with Whatman 3 filter paper. Leftovers from inside the flasks were washed with DW and passed through the filter. The filtrates were typically semi-milky and were filtered once more through the formed $Mg(OH)_2$ filter cakes to afford clear and colorless aqueous solutions. Each solution was transferred into a weighed round bottomed flask and water was evaporated to dryness using Rotovap to yield a white solid. After evaporation, the flasks were placed overnight at a desiccant under vacuum to discard residual water. Each flask was weighed again after complete drying and the total weight of the solids inside the flask was calculated. Then, the solids were dissolved in DW (250 mL) by stirring for at least 30 minutes at RT. The pH and conductivity of the solution were measured by a calibrated instrument. Lactate was measured using an enzymatic kit (Lactic Acid Test).

Procedure for Control Experiment (without $Mg(OH)_2$):

The experimental procedure described above was repeated under the same conditions but without addition of $Mg(OH)_2$. After filtration of PLA leftovers, the aqueous solution was not evaporated to dryness since no solid magnesium dilactate could be formed. Instead, the total volume of the filtrate was increased to 250 mL with DW and the pH, conductivity and lactate measurements were performed.

Figure 4:
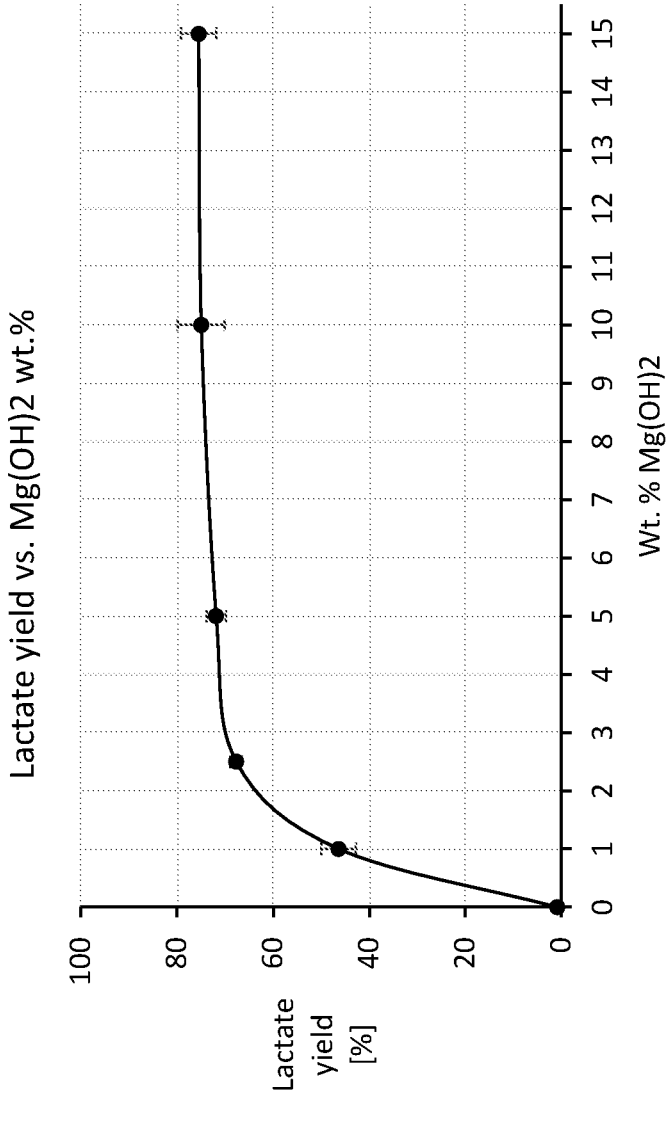
FIG. 4. Alkaline thermohydrolysis of thin-film PLA bags using magnesium hydroxide. Lactate yield vs. $Mg(OH)_2$ wt. %.

Results:

The results are summarized in Table 1 below and FIG. 4.

TABLE 1

| | | | | | | | |
|---|---|---|---|---|---|---|---|
| Hydrolysis of cut pieces of thin-film PLA bags by Mg(OH)$_2$ | | | | | | | |
| Mg(OH)$_2$ Wt. % | Weight of dried "white solid" [g] | In 250 mL DW pH | In 250 mL DW Cond. [mS] | Conc. lactate by kit* [g/L] | Weight of lactate in 250 mL [g] | 100% yield lactate ** [g] | Lactate yield |
| 0 | N/A | 2.9 | 235 | 0.228 ± 0.004 | 0.057 | 6.18 | 0.9% |
| 1 | 6.32 | 5.7 | 3.6 | 11.5 ± 0.9 | 2.875 | | 47% |
| 2.5 | 13.1 | 9.1 | 8.4 | 16.7 ± 0.3 | 4.175 | | 68% |
| 5 | 8.24 | 9.3 | 8.2 | 17.8 ± 0.5 | 4.450 | | 72% |
| 10 | 12.38 | 9.4 | 7.8 | 18.5 ± 1.2 | 4.625 | | 75% |
| 15 | repeat | 9.6 | repeat | 18.7 ± 0.9 | 4.675 | | 76% |

*The provided lactate concentration is an average of three measurements and the error is the relative standard deviation (RSD). The lactate concentration for the control experiment, where no Mg(OH)$_2$ was added, was measured using a ×10 dilution with DW since almost no PLA degradation occurred.
** The 100% yield calculation assumed that all PLA degraded to lactate units. Since each repeating unit of PLA weighs 72 Da and the lactate molecular weight is 89 Da, the overall weight must increase due to addition of a water molecule upon hydrolysis by a factor of 89/72 = 1.236. Accordingly, 5.0 g of PLA should give 5.0 × 1.236 = 6.18 g of lactate in case all the PLA was fully hydrolyzed. Hence, according to the 15 wt. % example above, 4.675 g lactate corresponds to (4.675/6.18) × 100% = 76% yield.
It is likely that low molecular weight oligomers of PLA still exist in the aqueous solution obtained after filtration of the hydrolysis suspension. It was contemplated that this is the reason for the clear solution that was observed. Yet not more than 76% yield was achieved.
It appears that 5 wt. % of Mg(OH)$_2$ provides a similar level of hydrolysis of PLA as 10 and 15 wt %., as evident by the similar amounts of lactate achieved for these concentrations of Mg(OH)$_2$.

Integration with a Lactic-Acid Production Lin:

The lactate-containing solution formed as a result of hydrolyzing in 5% Mg(OH)$_2$ was successfully added into an acidic (pH=5.5) lactic acid fermentation broth. The pH was increased to pH=6.8 and the solution was subjected to a downstream processing (DSP) procedure to produce pure magnesium lactate crystals as described in a co-pending patent application, WO 2020/110108, assigned to the Applicant of the present invention.

Example 2

Alkaline Thermohydrolysis of PLA Pellets using Sodium Hydroxide 50 g of PLA pellets (Ingeo™ Biopolymer 4032D, Nature-Works LLC.) were added to a 250 ml three-necked flask equipped with a condenser and a thermometer. 150 ml of NaOH 5M were added, and the flask was heated to 80° C. pH measured was 13.5.

After 3.5 hours of rapid degradation the concentration reached 320 g/L with only minor further increase in lactate concentration over time. After 21.5 hours, the lactate concentration stopped increasing (final concentration of 340 g/L) and the reaction was cooled to room temperature.

PLA residues were filtered using a sintered glass funnel to result in a clear solution. The final pH measured was 12.9 which is suitable for additional PLA degradation.

The solution was neutralized with concentrated H$_2$SO$_4$, then 280 ml of magnesium sulfate heptahydrate solution (300 g/L) were added dropwise while stirring. The MgLa$_2$·2H$_2$O precipitate that formed was filtered using a sintered glass funnel, washed with acetone, and dried at 80° C. to a final weight of 64 gr. The filtrate was added dropwise into 500 ml of acetone while stirring, and then stirred for another hour. The precipitate that formed was filtered using a sintered glass funnel, washed with acetone, and dried at 80° C. Yield: 74% yield.

The magnesium lactate precipitate is added into a lactic acid fermentation broth and subsequently subjected to a downstream processing (DSP) procedure to produce pure magnesium L-lactate crystals.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for producing an L-lactate salt from a combined recycling of polylactic acid (PLA) and organic waste, the method comprising the steps of:
   (a) hydrolyzing PLA waste with a metal oxide or a hydroxide to obtain a PLA hydrolysis slurry comprising L-lactate monomers and a first counterion;
   (b) fermenting organic waste with a lactic acid-producing microorganism in a fermenter in the presence of an alkaline compound to obtain a fermentation broth comprising L-lactate monomers and a second counterion, wherein the first and second counterions are the same; or wherein at least one of the first and second counterions is subjected to ion exchange thereby obtaining a first and second counterions which are the same;
   (c) optionally contacting the PLA hydrolysis slurry of step (a), the fermentation broth of step (b), or a mixture comprising the PLA hydrolysis slurry of step (a) and the fermentation broth of step (b) with a D-lactic acid degrading enzyme or a D-lactic acid-utilizing microorganism to eliminate D-lactate monomers thereby obtaining L-lactate monomers; and
   (d) purifying a mixture comprising the PLA hydrolysis slurry of step (a) and the fermentation broth of step (b) or the L-lactate monomers of step (c) thereby obtaining an L-lactate salt,
   wherein the mixture comprising the PLA hydrolysis slurry of step (a) and the fermentation broth of step (b) is obtained by adding the PLA hydrolysis slurry to the lactic acid fermenter during fermentation.

2. The method of claim 1, wherein step (a) is performed at a temperature in the range of about 50° C. to about 90° C. or wherein step (a) is performed for a period of time in the range of about 1 to about 12 hours or about 12 to about 36 hours.

3. The method of claim 1, wherein the metal oxide or hydroxide of step (a) and the alkaline compound of step (b) are the same compound.

4. The method of claim 1, wherein the first and second counterions are different.

5. The method of claim 4, wherein at least one of the hydroxide slurry of step (a) and the fermentation broth of step (b) are subjected to ion exchange thereby resulting in a first and second counterions which are the same.

6. The method of claim 1, wherein the metal oxide or alkaline compound comprise at least one of MgO, CaO, and a mixture or combination thereof.

7. The method of claim 1, wherein the hydroxide or alkaline compound comprise at least one of NaOH, KOH, $NH_4OH$, $Ca(OH)_2$, $Mg(OH)_2$, and mixture or combination thereof.

8. The method of claim 7, wherein the hydroxide is $Mg(OH)_2$.

9. The method of claim 1, wherein the lactate salt is magnesium L-lactate salt.

10. The method of claim 1, further comprising pretreatment of the PLA waste prior to step (a), wherein pretreatment comprises mechanical pretreatment selected from the group consisting of grinding, chipping, shredding, milling, and a combination thereof.

11. The method of claim 1, further comprising subjecting the PLA hydrolysis slurry obtained in step (a) to solid-liquid separation.

12. The method of claim 1, wherein the organic waste comprises endogenous D-lactic acid, L-lactic acid or both; or wherein the organic waste is selected from the group consisting of food waste, municipal waste, agricultural waste, plant material, and a mixture or combination thereof.

13. The method of claim 1, wherein the PLA waste comprises poly L-lactic acid (PLLA) and poly D-lactic acid (PDLA).

14. The method of claim 1, wherein step (c) is performed and wherein the D-lactic acid degrading enzyme in step (c) is a D-lactate oxidase.

15. The method of claim 1, wherein the obtained L-lactate salt is purified by at least one of crystallization, recrystallization, distillation, partitioning, silica gel chromatography, preparative HPLC, and combinations thereof.

16. The method of claim 1, wherein the obtained L-lactate salt is acidified to form L-lactic acid for subsequent poly-lactic acid formation.

* * * * *